United States Patent [19]

Kanno et al.

[11] Patent Number: 4,758,558
[45] Date of Patent: Jul. 19, 1988

[54] N-(SUBSTITUTED)-[7-(2-CYANOACETAMIDO)CEPHALOSPORANIC-]AMIDE DERIVATIVES HAVING ANTIBIOTIC UTILITY

[75] Inventors: Akihiko Kanno; Shigeaki Muto, both of Tokyo; Koichi Niimura, Sayama; Takao Ando; Takayoshi Fujii, both of Tokyo; Masahiko Fujii, Komae; Takao Furusho, Machida; Chikao Yoshikumi, Kunitachi, all of Japan

[73] Assignee: Kureha Kagaku Kogyo Kabushiki Kaisha, Tokyo, Japan

[21] Appl. No.: 864,574

[22] Filed: May 19, 1986

Related U.S. Application Data

[63] Continuation of Ser. No. 563,514, Dec. 20, 1983, abandoned.

[30] Foreign Application Priority Data

Dec. 29, 1982 [JP] Japan ................. 57-234549
Dec. 29, 1982 [JP] Japan ................. 57-234551
Dec. 29, 1982 [JP] Japan ................. 57-234553

[51] Int. Cl.$^4$ ............... A61K 31/545; C07D 501/26; C07D 501/36; C07D 501/22
[52] U.S. Cl. ................. 514/207; 514/202; 514/204; 540/223; 540/226; 540/227
[58] Field of Search ............ 540/223, 227, 226; 514/202, 204, 207

[56] References Cited

U.S. PATENT DOCUMENTS

| 3,124,576 | 3/1964 | Stedman | 544/30 |
| 3,338,897 | 8/1967 | Takano et al. | 544/30 |
| 3,483,197 | 12/1969 | Bickel et al. | 544/30 |
| 3,641,015 | 2/1972 | Lewis et al. | 540/228 |
| 4,045,437 | 8/1977 | Barth | 540/217 |
| 4,496,561 | 1/1985 | Muto et al. | 544/23 |

FOREIGN PATENT DOCUMENTS

| 75451 | 3/1983 | European Pat. Off. | 544/30 |
| 0075450 | 3/1983 | European Pat. Off. | |
| 2027793 | 3/1927 | Japan | 544/30 |
| 6083493 | 7/1981 | Japan | 544/30 |
| 6087585 | 7/1981 | Japan | 544/30 |

OTHER PUBLICATIONS

Greene, Theodora, *Protective Groups in Organic Synthesis*, John Wiley, New York (1981) p. 182.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

Disclosed herein are the derivatives of substituted cephalosporanic acid represented by the formula (I):

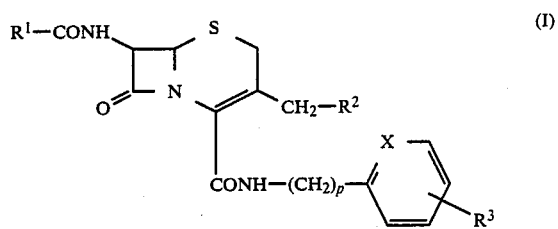

wherein $R^1$ represents a 4-pyridylthiomethyl group, an alpha-aminobenzyl group, a cyanomethyl group or a 1-tetrazolylmethyl group; $R^2$ represents a hydrogen atom, an acetoxy group or a (5-methyl-1,3,4-thiadiazol-2-yl)thio group; $R^3$ represents a hydrogen atom, a hydroxyl group, a carbamoyl group, an alkyl group having 1 to 4 carbon atoms or $-(CONH)_m(CH_2)_n-COOH$ wherein m is 0 or 1, n is 0, 1 or 2 and the carboxyl group may have been converted to a salt or an ester thereof; p is 0, 1 or 2 and X represents carbon atom or nitrogen atom, and antibiotics comprising the derivatives of substituted cephalosporanic acid represented by the formula (I).

12 Claims, No Drawings

N-(SUBSTITUTED)-[7-(2-CYANOACETAMIDO)-CEPHALOSPORANIC]AMIDE DERIVATIVES HAVING ANTIBIOTIC UTILITY

This application is a continuation of application Ser. No. 563,514, filed Dec. 20, 1983, now abandoned.

BACKGROUND OF THE INVENTION

The present invention relates to derivatives of substituted cephalosporanic acid and antibiotics comprising the derivatives of cephalosporanic acid. More in detail, the present invention relates to the derivatives of substituted cephalosporanic acid, represented by the formula (I):

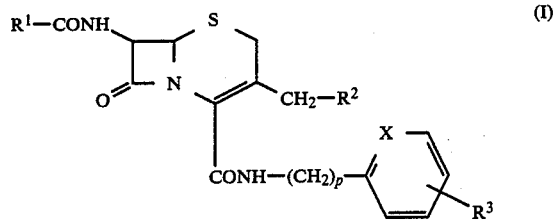

wherein $R^1$ represents a 4-pyridylthiomethyl group

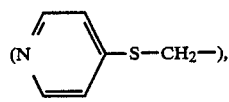

an alpha-aminobenzyl group

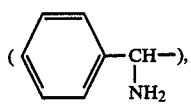

a cyanomethyl group ($N\equiv C-CH_2-$) or a 1-tetrazolylmethyl group

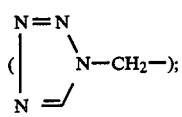

$R^2$ represents a hydrogen atom, an acetoxy group or a (5-methyl-1,3,4-thiadiazol-2-yl)thio group

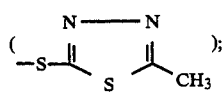

$R^3$ represents a hydrogen atom, a hydroxyl group, a carbamoyl group, an alkyl group having 1 to 4 carbon atoms or $-(CONH)_m(CH_2)_n-COOH$ wherein m is 0 or 1; n is 0, 1 or 2 and the carboxyl group may have been converted to a salt or an ester thereof; p is 0, 1 or 2 and X represents carbon atom or nitrogen atom and the antibiotics comprising the derivatives of substituted cephalosporanic acid, represented by the formula (I).

The derivatives of substituted cephalosporanic acid according to the present invention (hereinafter referred to as the present compounds) are the novel antibiotics of quite a new type in the sense that each of the present compounds has been obtained by chemically modifying a conventional antibiotic comprising a substituted cephalosporanic acid, and although the antibiotic property of the parent compound has been lost by the chemical modification, the once-lost antibiotic property is exhibited by the present compound after it is absorbed into living body of the host to which the present compound has been administered.

Antibiotics comprising substituted cephalosporanic acid, so-called, cephalosporins, are now broadly used because of their favorable antibiotic property and of their fairly high selective activity against noxious bacterial species, however, because of their activity also against useful bacterial species habitually present in living body of the host to which the antibiotic is to be administered, such an antibiotic has a serious demerit of disturbing the useful intestinal bacterial colonies when it is orally administered to the host resulting in causing colitis or diarrhea on the host in some cases.

The present inventors have found, after studying for obtaining antibiotics which do not have such a demerit and still exhibit the antibiotic activity against noxious bacteria, that the derivatives of substituted cephalosporanic acid, represented by the formula (I) are quite suitable for the object of the present inventors, and they have attained the present invention.

Accordingly, the object of the present invention is to provide the derivatives of substituted cephalosporanic acid, which never disturb the intestinal bacterial colonies while exhibiting an excellent antibiotic activity against noxious bacteria.

SUMMARY OF THE INVENTION

In the first aspect of the present invention, there are provided the derivatives of substituted cephalosporanic acid represented by the formula (I):

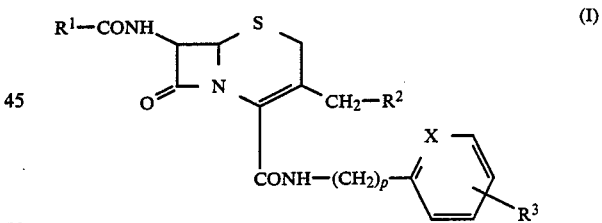

wherein $R^1$ represents a 4-pyridylthiomethyl group

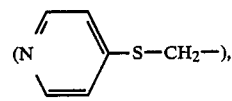

an alpha-aminobenzyl group

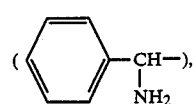

a cyanomethyl group ($N\equiv C-CH_2-$) or a 1-tetrazolylmethyl group

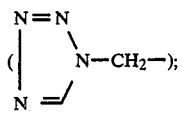

R² represents a hydrogen atom, an acetoxy group or a (5-methyl-1,3,4-thiadiazol-2-yl)thio group

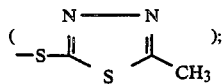

R³ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted into a salt or an ester thereof; p is 0, 1 or 2 and X represents carbon atom or nitrogen atom.

In the second aspect of the present invention, there is provided a process for producing the derivative of substituted cephalosporanic acid, represented by the formula (I), comprising reacting a substituted cephalosporanic acid represented by the formula (II):

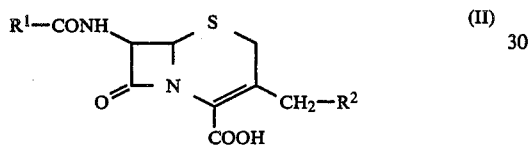

wherein R¹ and R² respectively represent the same group as in the formula (I), with a compound represented by the formula (III):

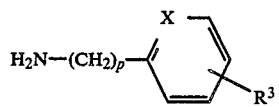

wherein R³ represents a hydrogen atom, a hydroxyl group, a carbamoyl group, an alkyl group of 1 to 4 carbon atoms or —(CONH)$_m$(CH$_2$)$_n$—COOH wherein m is 0 or 1, n is 0, 1 or 2 and the carboxylic acid may have been converted to a salt or an ester thereof, p is 0, 1 or 2 and X represents carbon atom or nitrogen atom in a solvent at −30° to 50° C. for 0.5 to 48 hours.

In the third aspect of the present invention, there are provided the antibiotics comprising the derivative of substituted cephalosporanic acid represented by the formula (I):

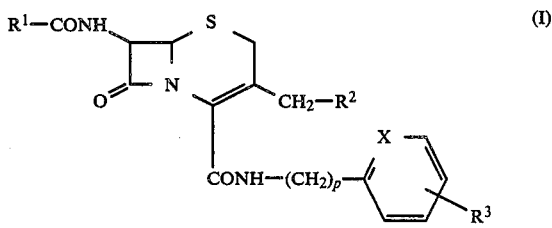

wherein R¹ represents a 4-pyridylthiomethyl group

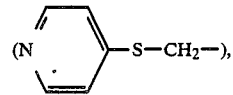

an alpha-aminobenzyl group

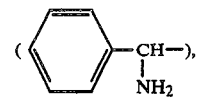

a cyanomethyl group (N≡C—CH$_2$—) or a 1-tetrazolylmethyl group

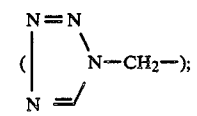

R² represents a hydrogen atom, a (5-methyl-1,3,4-thiadiazol-2-yl)thio group

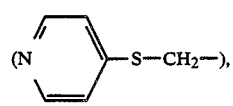

or an acetoxy group; R³ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted into a salt or an ester thereof; p is 0, 1 or 2 and X represents carbon atom or nitrogen atom.

In the fourth aspect of the present invention, there are provided the pharmaceutical compositions in dosage unit form comprising an effective dosage of the derivative of substituted cephalosporanic acid, represented by the formula (I):

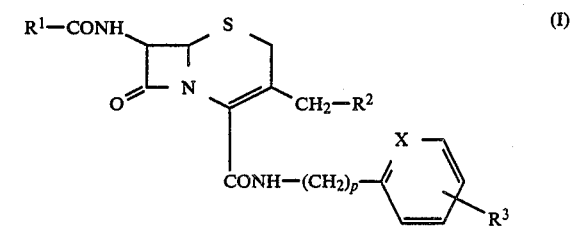

wherein R¹ represents a 4-pyridylthiomethyl group

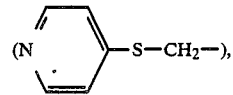

an alpha-aminobenzyl group

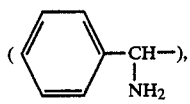

a cyanomethyl group (N≡C—CH₂—) or a 1-tetrazolylmethyl group

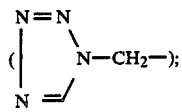

$R^2$ represents a hydrogen atom, an acetoxy group or a (5-methyl-1,3,4-thiadiazol-2-yl)thio group

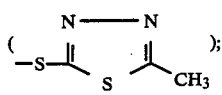

$R^3$ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted to a salt or an ester thereof; p is 0, 1 or 2 and X represents carbon atom or nitrogen atom as an active ingredient and a pharmaceutically acceptable carrier.

In the fifth aspect of the present invention, there is provided a method for treatment of infectious diseases caused by bacteria, comprising administering to the host suffering from the infectious disease an effective amount of the derivative of substituted cephalosporanic acid represented the formula (I):

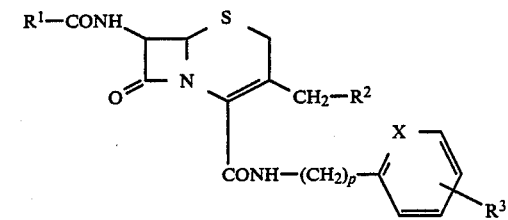

wherein $R^1$ represents a 4-pyridylthiomethyl group

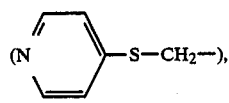

an alpha-aminobenzyl group

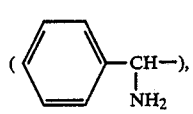

a cyanomethyl group (N≡C—CH₂—) or a 1-tetrazolylmethyl group

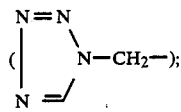

$R^2$ represents a hydrogen atom, an acetoxy group or a (5-methyl-1,3,4-thiadiazol-2-yl)thio group

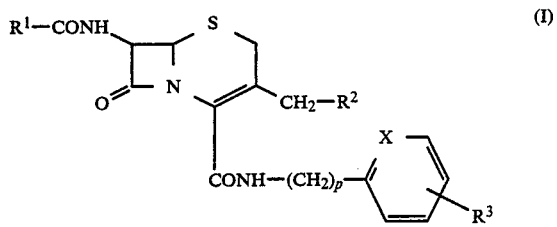

$R^3$ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted into a salt or an ester thereof; p is 0, 1 or 2 and X represents carbon atom or nitrogen atom.

DETAILED EXPLANATION OF THE INVENTION

The present invention relates to the derivatives of substituted cephalosporanic acid, represented by the formula (I):

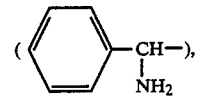

wherein $R^1$ represents a 4-pyridylthiomethyl group

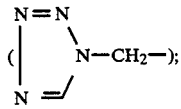

an alpha-aminobenzyl group a cyanomethyl group (N≡C—CH₂—) or a 1-tetrazolylmethyl group $R^2$ represents a hydrogen atom, an acetoxy group or a (5-methyl-1,3,4-thiadiazol-2-yl)thio group

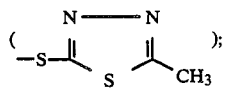

$R^3$ represents a hydrogen atom, a hydroxyl group, a carbamoyl group, an alkyl group having 1 to 4 carbon atoms or —(CONH)$_m$(CH$_2$)$_n$—COOH wherein m is 0 or 1; n is 0, 1 or 2 and the carboxyl group may have been converted into a salt or an ester thereof; p is 0, 1 or 2 and X represents carbon atom or nitrogen atom.

Each compound represented by the formula (I) has been obtained by chemically modifying an antibiotic which is a substituted cephalosporanic acid, and when the thus modified compound is administered to the host, it is absorbed into living body of the host without affecting the bacteria habitually present in living body of the host and it exhibits an antibacterial activity after having entered into the blood of the host. Namely, the compounds represented by the formula (I) are the antibiotics of quite a new type, and in addition, each of them shows an extremely low acute mammalian toxicity which supports the safety of the derivatives of substituted cephalosporanic acid according to the present invention.

The present compound, that is, a derivative of substituted cephalosporanic acid represented by the formula (I) is obtained by the following process.

Namely, a compound represented by the formula (II), that is, a substituted cephalosporanic acid:

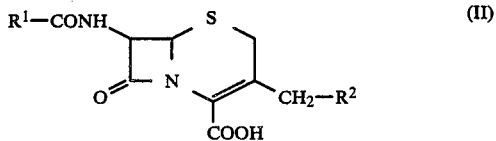

wherein $R^1$ represents a 4-pyridylthiomethyl group, an alpha-aminobenzyl group, a cyanomethyl group or a 1-tetrazolylmethyl group and $R^2$ represents a hydrogen atom, an acetoxy group or a (5-methyl-1,3,4-thiadiazol-2-yl)thio group is reacted with a compound represented by the formula (III):

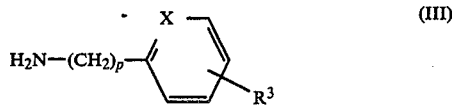

wherein p is 0, 1 or 2, X represents carbon atom or nitrogen atom and $R^3$ represents a hydrogen atom, a hydroxyl group, a carbamoyl group, an alkyl group having 1 to 4 carbon atoms or —(CONH)$_m$(CH$_2$)$_n$—COOH wherein m is 0 or 1, n is 0, 1 or 2 and the carboxylic group may have been converted into a salt or an ester thereof usually in a solvent preferably at a temperature of $-30°$ to $50°$ C. for 0.5 to 48 hours.

Instead of the compound represented by the formula (II), a reactive derivative of the compound represented by the formula (II) may be used in the reaction with the compound represented by the formula (III), and as such a reactive derivative, acid chloride, acid bromide, acid azide, mixed anhydride with alkylphosphoric acid, mixed anhydride with alkylcarbonic acid, mixed anhydride with an aliphatic carboxylic acid, anhydride, an alkali metal salt, an alkaline earth metal salt, ammonium salt and a salt of trimethylamine or dicyclohexylamine of the compound represented by the formula (II) may be mentioned.

In addition, instead of the compound represented by the formula (III), a hydrochloride or hydrobromide of the compound represented by the formula (III) may be used in the reaction with the compound represented by the formula (II) or the reactive derivative thereof.

As the compound represented by the formula (III), for instance, 4-aminophenylacetic acid, 3-aminophenylacetic acid, 2-aminophenylacetic acid, 4-toluidine, 3-toluidine, 2-toluidine, 4-aminohippuric acid, thylamine, 4-aminobenzoic acid, 3-aminobenzoic acid, 2-aminobenzoic acid, 4-aminosalicylic acid, 3-aminosalicylic acid, 2-aminosalicylic acid, 6-aminonicotinic acid, and 2-aminonicotinic acid and salts thereof and esters thereof may be mentioned.

Although as the solvent, acetone, tetrahydrofuran, benzene, dichloromethane, dioxane, acetonitrile, ethylene dichloride, chloroform, ethyl acetate, ethyl formate, diethyl ether or dimethylformamide is used, any solvent may be used unless it participates with the reaction. The above-mentioned solvents, any one of those which are soluble in water may be used after being mixed with water as an aqueous solvent.

Furthermore, it is preferable to add carbodiimide, ethyl chlorocarbonate, ethyl chloroformate, oxalyl chloride, quinoline, alkali metal hydrogencarbonate, trialkylamine, dialkylaniline or pyridine into the reaction system.

After the reaction is over, the protective group for the amino group on the product is removed according to the demand, and the object product is collected from the reaction mixture by means of washing the product with a solvent, extracting the product with a solvent, separating by using a chromatographic column, reprecipitation of the product, distilling the solvent off from the reaction mixture, crystallizing including recrystallizing, etc.

The salts and the esters of the present compound represented by the formula (I) may be pharmaceutically acceptable salts and esters. In addition, after synthesizing the present compound represented by the formula (I), it may be converted to the salt or to the ester thereof by the conventional method. As the pharmaceutically acceptable salt, sodium salt, potassium salt, calcium salt, triethylamine salt, dicyclohexylamine salt and salt of basic amino acid such as arginine, ornithine, lysine or histidine may be mentioned.

As the ester of the compound represented by the formula (I), $C_1$ to $C_4$-alkyl esters such as methyl ester, ethyl ester, propyl ester and butyl ester, $C_1$ to $C_4$-alkoxymethyl esters such as methoxymethyl ester, ethoxymethyl ester and isopropyloxymethyl ester, $C_1$ to $C_4$ alkoxy-(substituted methyl) esters such as alpha-methoxyethyl ester, alpha-ethoxyethyl ester and alpha-$C_1$ to $C_4$-alkoxyethyl ester, $C_1$ to $C_4$-alkylthiomethyl esters such as methylthiomethyl ester, ethylthiomethyl ester, isopropylthiomethyl ester, acyloxymethyl esters such as pivaloyloxymethyl ester, alpha-acetoxybutyl ester and acyloxy-(substituted methyl) ester may be mentioned.

Pharmacological properties of the present compounds were investigated as follows:

(a) Acute mammalian toxicity:

Acute mammalian toxicity of the present compound was determined by orally or intraperitoneally administering a series of suspensions of each of the present compounds in aqueous physiological saline solution to groups of ICR-JCL mice, and observing the toxic symptoms including mortality of the thus treated mice for 7 days. From the cumulative mortality and the concentrations of the aqueous suspension of each of the present compounds, $LD_{50}$ value was obtained by Litchfield-Wilcoxson's graphical method of calculation.

As the result, both $LD_{50}$ (oral) value and $LD_{50}$ (intraperitoneal) value of each of the present compound were higher than 10 g/kg body weight of the mouse (average).

(b) Effect on the intestinal bacterial colonies:

After collecting the feces of a group of mice, each of the present compounds was orally administered thereto for 2 days at a daily dose of 100 mg/kg body weight and the feces were collected one day after the 2 days. Each portion of the two kinds of the feces was cultured at 25° C. or 37° C. in a variety of culture medium for one to five days to see the state of *Escherichia coli*, *Pseudomonas aeruginosa*, a Streptococcus species, a Lactobacillus species, *Lactobacillus bifidus* and a Bacteroides species in the culture medium.

As the result, no substantial difference was found between the number of cells of each bacterial species before the administration of each of the present compounds and that after the administration thereof, the result telling that each of the present compounds tested herein gives no effect on the intestinal bacterial colonies in living body of the mouse. (Refer to Example 19 for the details of the test.)

(c) Anti-bacterial activity (in vitro):

Minimum concentration of the present compound inhibiting the growth of the following bacteria was determined according to the standard procedures of Japan Society of Chemotherapy:

*Escherichia coli* IFO 12734 and
*Staphylococcus aureus* IAM 1011

(Refer to Example 20 for the details of the test including the thus obtained minimum concentration of each of the present compounds tested inhibiting the growth of the bacteria (referred to as MIC).)

(d) Antibacterial activity in the presence of rat-liver homogenate:

In order to preliminarily determine whether the present compound becomes actually antibiotic after being absorbed into living body of the host to which the present compound has been administered or not, the following test was carried out.

On each of the flat culture plates prepared by adding a cultured liquid containing $10^8$ cells/ml of the preliminarily cultured *Staphylococcus aureus* IAM 1011 to 50 times by weight of Mueller-Hinton's culture medium, a penicillin cup of 8 mm in diameter was placed, and after adding 0.1 ml of each of the aqueous dispersions of each of the present compounds at respective concentrations or 0.1 ml of each of the preliminarily cultured solution of rat-liver homogenate (containing a metabolism-activating enzyme) containing each of the present compounds at the same concentration as above into the penicillin cup, the flat culture plates were incubated for 18 hours at 37° C. Thereafter, the diameter of the growth-inhibiting circle appearing around the cup was measured. (Refer to Example 21 for the details of the test.)

As the result, when the value of the diameter of growth-inhibiting circle due to the substituted cephalosporanic acid used as the starting material for producing the present compound was represented by 100, the value of the diameter of growth-inhibition only due to each of the present compound (that is, without containing the preliminarily cultured rat-liver homogenate) was zero, and on the other hand, the value of the diameter of growth-inhibiting circle due to each of the present compounds plus the preliminarily cultured rat-liver homogenate was 1 to 66.

The result strongly suggests that each of the present compounds will become antibitic after entering into living body of the host to which each of the present compounds has been administered.

(e) Effectiveness in treating experimental infectious disease due to bacteria:

In order to confirm the above-mentioned suggestion concerning the in vivo activation of the present compound to be antibiotic, the following experimental treatment was carried out on the artificially infected animals by the respective two bacterial species. (Refer to Example 22 for the details of the test.) As the result, while all the twenty mice artificially infected with each of the two bacterial species and not-treated with any of the present compound died on the second day of inoculation, more than 40% of the twenty mice artificially infected with each of the two bacterial species and administered with each of the three present compounds were alive even after 7 days of inoculation.

As will be seen in the above-mentioned pharmacological properties of the present compounds, it may be said that the present compounds are safe for medical use and are quite the new type of an antibiotic substance in the sense that the present compounds themselves do not exhibit any anti-bacterial properties as they are, however, they are activated to be antibiotic after being absorbed in living body of the host probably by the action of a metabolism-activating enzyme in living body, particularly in the blood.

Accordingly, it is rationally considered that the present compound is converted to an antibiotic substance of the chemical structure closely related to that of the substituted cephalosporanic acid which is used as the starting material in the present invention and is itself an antibiotic, and the present compound can be used as an antibiotic in the same field in which cephalosporins are now used, and is actually effective against bacteria in a broad range including gram-positive and gram-negative bacteria.

The present compound can be used in the form of pharmaceutical compositions in dosage unit form thereof comprising at least one of the present compounds as the active ingredient, a pharmaceutically acceptable carrier, pharmaceutically acceptable diluent or pharmaceutically acceptable adjuvant, which can be administered orally, injectionally or rectally. Particularly, oral administration may be carried out in the form of powders, granules, pellets and ampoules. The adjuvant includes fillers, extenders, binding agents, wetting agents, disintegrators, dissolution-retarders, accelerators for re-absorption, adsorbing carriers, lubricators, etc., and as the definite instance thereof, starch, mannitol, silicic acid, derivatives of cellulose, gelatin, alginate salts, glycerol, agar, calcium carbonate, sodium hydrogencarbonate, paraffin, quaternary ammonium compound, glycerol monostearate, kaolin, bentonite, talc, potassium stearate, magnesium stearate and polyethylene glycol may be mentioned. In addition, the above-mentioned pharmaceutical composition may take the form of a pharmaceutically acceptable emulsion, pharmaceutically acceptable solution in a solvent or suspension.

Suppository comprising the present compound may contain polyethylene glycol, fatty acids or esters thereof.

Syrups and elixirs comprising the present compound contain an inert diluent such as water or paraffin and can be used as a liquid composition suitable for oral administration.

Compositions comprising the present compound used for injection should be aseptic and may be an aqueous or nonaqueous solution, suspension or emulsion, and may contain, for instance, propylene glycol, polyethylene glycol and olive oil.

In the case where the present compound is used in the form of a pharmaceutical composition as an active ingredient, the content thereof may be 0.01 to 99.5% by weight, usually 0.1 to 90% by weight.

The present compound is used in the same field in which the so-called cepharosporin antibiotics are used, and is effective in treatments of infectious disease caused by bacteria at a daily dosage of 0.1 to 10 g per an adult human patient, which is divided and portionally taken in several times a day, of course depending on the degree of infection and the state of the patient.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

Production of
N-(4-carbomethoxyphenyl)-[7-beta-(4-pyridylthioacetamido)cephalosporanic]amide In 10 ml of acetone, 445 mg of sodium 7-(4-pyridylthioacetamido)cephalosporanate were suspended, and after adding three drops of pyridine into the suspension, 217 mg of ethyl chlorocarbonate were added to the suspension, and the mixture was stirred for 30 min at 0° C. Thereafter, 151 mg of methyl 4-aminobenzoate were added to the thus stirred mixture, and the mixture was stirred for 30 hours at 20° C. After the reaction was over, the solvent was distilled off from the reaction mixture, and after adding 30 ml of aqueous 1% solution of sodium hydrogencarbonate to the distillation residue, the mixture was extracted three times with each 30 ml of ethyl acetate. After washing the combined extracts with 30 ml of aqueous 0.1N hydrochloric acid solution, the extract was washed with 30 ml of water, and after drying the ethyl acetate layer on anhydrous sodium sulfate and filtering the dried layer with a sheet of filter paper, the filtrate was dried under a reduced pressure to obtain a crude product, which was recrystallized from a mixture of ethyl acetate and n-hexane to obtain 132 mg of the object product as crystals melting at 140° to 141° C. in a yield of 23.7%.

The thus obtained product of a chemical structure shown below showed an infrared absorption spectrum with the following absorption maxima(cm$^{-1}$) as a KBr-tablet and an ultraviolet absorption spectrum with the following absorption maxima(nm)

IR maxima: 3325, 2900, 2825, 1780, 1760, 1680, 1620, 1595, 1520 and 1280

UV maxima: 218 and 278.

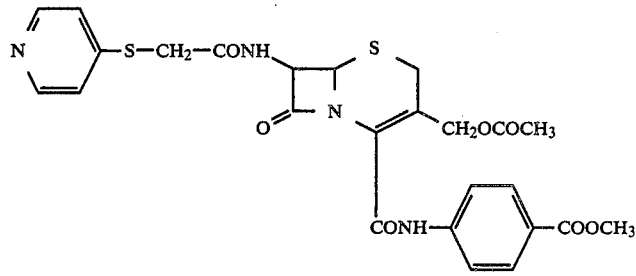

The product showed the following elementary analytical data:

|  | C (%) | H (%) | N (%) |
| --- | --- | --- | --- |
| Found: | 53.8 | 4.2 | 10.0 |
| Calcd. as C$_{25}$H$_{24}$N$_4$O$_7$S$_2$: | 53.95 | 4.35 | 10.07 |

EXAMPLE 2

Production of
N-(4-carbomethoxymethylphenyl)-[7-(4-pyridylthioacetamido)caphalosporanic]amide In quite the same procedures as in Example 1, except for using 165 mg of methyl 4-aminophenylacetate instead of 151 mg of methyl 4-aminobenzoate in Example 1, 136 mg of the object product were obtained as crystals melting at 99° to 100° C. in a yield of 24%.

The thus obtained product showed an infrared spectrum with the following absorption maxima as a KBr-tablet and an ultraviolet absorption spectrum with the following absorption maxima in methanol:

IR Max.: 3350, 2925, 2850, 1780, 1690, 1650, 1520 and 1220 cm$^{-1}$

UV Max.: 215 and 258 nm.

The elementary analytical data of the product were as follows:

|  | C (%) | H (%) | N (%) |
| --- | --- | --- | --- |
| Found: | 54.6 | 4.6 | 9.8 |
| Calcd. as C$_{26}$H$_{26}$N$_4$O$_7$S$_2$: | 54.72 | 4.59 | 9.82 | corresponding to the following chemical structure:

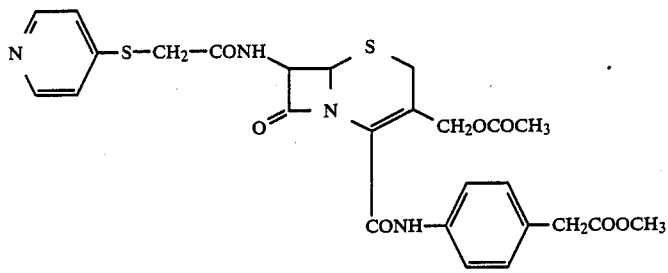

EXAMPLE 3

Production of
N-(4-carbomethoxymethylcarbamoylphenyl)-[7-(4-pyridylthioacetamido)cephalosporanic]amide A solution of 423.4 mg of 7-(4-pyridylthioacetamido)-cephalosporanic acid, 208.2 mg of methyl 4-aminohippurate and 206 mg of N,N'-dicyclohexylcarbodiimide in 50 ml of tetrahydrofuran was stirred for 24 hours at 20° C., and after removing the thus formed N,N'-dicyclohexylurea by filtering the reaction mixture, the solvent was distilled off from the filtrate, and the residue was dissolved in 50 ml of chloroform. After washing the solution with aqueous 5% hydrochloric acid solution and then with water, the washed solution was dried on anhydrous magnesium sulfate, and after distilling the solvent off from the dried solution, the residue was recrystallized from a mixture of ethyl acetate and n-hexane to obtain 319 mg of crystals of the object product melting at 87° to 89° C. in a yield of 52%.

The product showed an infrared absorption spectrum as a KBr-tablet with the following absorption maxima and an ultraviolet absorption spectrum in methanol with the following absorption maxima:

IR Max.: 3350, 2930, 2850, 1790, 1705, 1640 and 1520 cm$^{-1}$

UV Max.: 225 and 270 nm.

The elementary analytical data of the product were as follows:

|  | C (%) | H (%) | N (%) |
| --- | --- | --- | --- |
| Found: | 52.8 | 4.4 | 11.3 |
| Calcd. as $C_{27}H_{27}O_8N_5S_2$: | 52.85 | 4.43 | 11.41 | corresponding to the chemical structure as follows:

EXAMPLE 4

Production of
N-(4-carbomethoxymethylphenyl)-[7-(D-alpha-aminophenylacetamido)desacetoxycephalosporanic]amide A solution of 4.42 g of 7-(D-alpha-aminophenylacetamido)desacetoxycephalosporanic acid, 1.65 g of methyl 4-aminophenylacetate and 2.10 g of N,N'-dicyclohexylcarbodiimide in 70 ml of tetrahydrofuran was stirred for 14 hours at 30° C. After collecting the crystals formed in the reaction mixture and washing the collected crystals with 30 ml of tetrahydrofuran, the crystals were recrystallized from ethanol to obtain 3.4 g of white crystalline powder of N-(4-carbomethoxymethylphenyl)-7-(alpha-tert-butoxycarbonyl-aminophenylacetamido)desacetoxycephalosporanic amide in a yield of 58% which showed the following infrared absorption maxima as a KBr-tablet:

3320, 1790, 1735, 1672, 1535, 1371 and 1170 cm$^{-1}$.

Thereafter, to 2.9 g of the thus obtained white crystals, 10 ml of trifluoroacetic acid were added, and the mixture was stirred for one hour at room temperature. After distilling excess trifluoroacetic acid from the reaction mixture under a reduced pressure, the thus obtained residue was extracted with 100 ml of ethyl acetate. After washing the extract two times with aqueous 5% solution of sodium hydrogencarbonate and then once with water, the extract was dried on anhydrous magnesium sulfate, and after distilling the solvent off from the extract, the residue was recrystallized from a mixture of ethyl acetate and n-hexane to obtain 1.5 g of white crystalline powder melting at 194° to 195° C. in a yield of 61%. The thus obtained final product showed the following infrared absorption maxima as a KBr-tablet and the following ultraviolet absorption maxima in methanol:

IR: 3320, 1768, 1728, 1665, 1530 and 1660 cm$^{-1}$

UV: 226 and 267 nm.

The final product gave the following elementary analytical data:

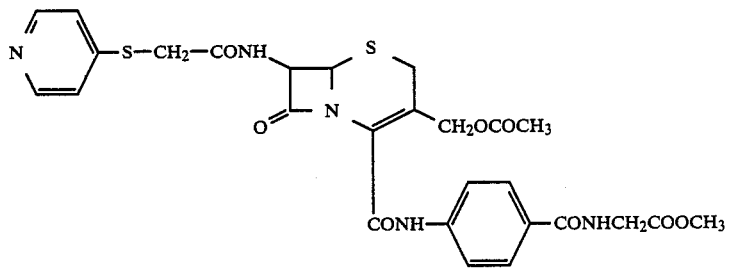

|   | C (%) | H (%) | N (%) |
|---|---|---|---|
| Found: | 60.7 | 5.2 | 11.3 |
| Calcd. as $C_{25}H_{26}N_4O_5S$: | 60.73 | 5.26 | 11.34 | corresponding to the chemical structure shown below:

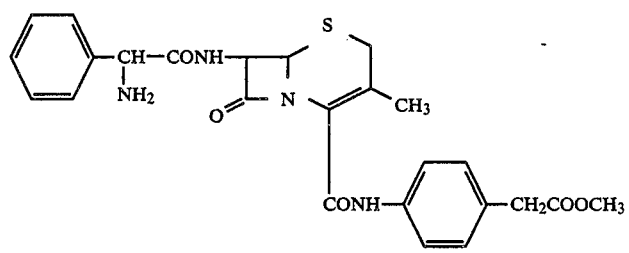

EXAMPLE 5

Production of N-(4-carbomethoxymethylcarbamoylphenyl)-[7-(D-alpha-aminophenylacetamido)desacetoxycephalosporanic]amide In quite the same procedures as in Example 4 except for using 4.42 g of 7-(alpha-tert-butoxycarbonylaminophenylacetamido)desacetoxycephalosporanic acid and 2.08 g of methyl 4-aminohippurate instead respectively of 4.42 g of 7-(D-alpha-aminophenylacetamido)-desacetoxycephalosporanic acid and 1.65 g of methyl 4-aminophenylacetate in Example 4, 3.2 g of N-(4-carbomethoxymethylcarbamoylphenyl)-[7-(alpha-tert-butoxycarbonylaminophenylacetamido)desacetoxycephalosporanic]amide as crystalline powder were obtained in a yield of 51%. The product showed the following infrared absorption maxima as a KBr-tablet:

3300, 1790, 1745, 1640, 1525 and 1370 $cm^{-1}$.

The thus obtained product was amounting to 3.16 g treated by the same procedures as in Example 4 to give 1.3 g of the object product of pale yellow powdery crystals melting at 170° to 172° C., which showed the following infrared absorption maxima as a KBr-tablet, and the following ultraviolet absorption maxima in methanol:

IR Max.: 3280, 1778, 1724, 1660, 1530 and 1214 $cm^{-1}$
UV Max.: 224, 265 and 282 nm The elementary analytical data of the object product were:

|   | C (%) | H (%) | N (%) |
|---|---|---|---|
| Found: | 58.1 | 5.1 | 13.0 |
| Calcd. as $C_{26}H_{27}N_5O_6S$: | 58.10 | 5.03 | 13.04 | corresponding to the chemical structure shown below:

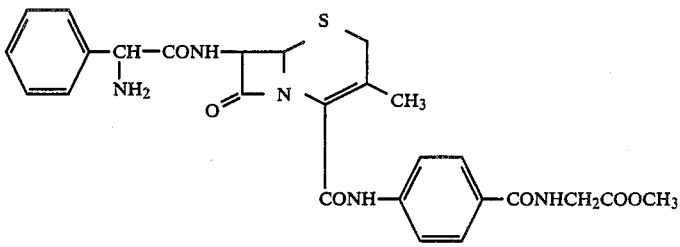

EXAMPLE 6

Production of N-(nicotinamido)-[7-(4-pyridylthioacetamido)cephalosporanic acid]amide A solution of 423.45 mg of 7-(4-pyridylthioacetamido)cephalosporanic acid, 137.1 mg of 6-aminonocotinic acid amide and 206 mg of N,N'-dicyclohexylcarbodiimide in 30 ml of dimethylformamide was stirred for 24 hours at room temperature. The white precipitate which was obtained when the thus stirred solution was introduced into 500 ml of water was collected by centrifugation and then dissolved in ethyl acetate. After drying the solution under a reduced pressure, acetone was added to the residue, and the insoluble matter in acetone was discarded. By drying the remaining liquid matter under a reduced pressure, a crude product was obtained and it was recrystallized from a mixture of acetone and n-hexane to obtain 219 mg of the object product as pale yellow powdery crystals melting at 108° to 109° C. in a yield of 40.4%, which gave the following infrared absorption maxima as a KBr-tablet, and the following ultraviolet absorption maximum in methanol:

IR Max.: 3390, 2950, 2880, 1801, 1710, 1655, 1525, 1390 and 1235 $cm^{-1}$
UV Max.: 260 nm The object product gave the following elementary analytical data:

|   | C (%) | H (%) | N (%) |
|---|---|---|---|
| Found: | 50.7 | 4.1 | 15.6 |
| Calcd. as $C_{23}H_{22}N_6O_6S_2$: | ˙50.91 | 4.09 | 15.49 | corresponding to the chemical structure shown below:

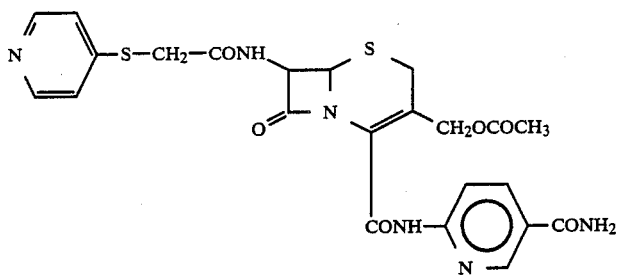

EXAMPLE 7

Production of N-(4-carbomethoxyphenyl)-[7-(2-cyanoacetamido)-cephalosporanic]amide In the same procedures as in Example 1 except for using 361.3 mg of sodium 7-(2-cyanoacetamido)cephalosporanate instead of 445 mg of sodium 7-(4-pyridylthioacetamido)cephalosporanate in Example 1 and stirring for 24 hours at 20° C. instead of stirring for 30 hours at 20° C. in Example 1, 30 mg of crystals melting at 228° to 229° C. of the object product were obtained in a yield of 6%.

The object product gave the following infrared absorption maxima as a KBr-tablet and the following ultraviolet absorption maximum in methanol:

IR Max.: 3270, 3060, 2975, 1770, 1720, 1660, 1600 and 1530 cm$^{-1}$
UV Max.: 285 nm.

The elementary analytical data of the object product were as follows:

|  | C (%) | H (%) | N (%) |
|---|---|---|---|
| Found: | 53.4 | 4.2 | 11.7 |
| Calcd. as $C_{21}H_{20}N_4O_7S$: | 53.38 | 4.27 | 11.86 | corresponding to the chemical structure shown below:

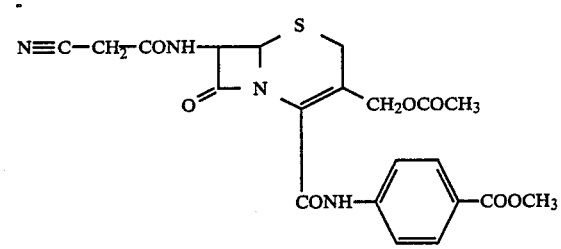

EXAMPLE 8

Production of N-(4-carbomethoxymethylphenyl)-7-[(2-cyanoacetamido)cephalosporanic]amide In the same procedure as in Example 1 except for using 361.3 mg of sodium 7-(2-cyanoacetamido)cephalosporanate and 165 mg of methyl 4-aminophenylacetate, respectively instead of 445 mg of sodium 7-(4-pyridylthioacetamido)cephalosporanate and 151 mg of methyl 4-aminobenzoate in Example 1 and stirring the mixture at 10° C. for 30 hours instead of 20° C. for 30 hours in Example 1, 115 mg of crystals of the objects product melting at 109° to 111° C. were obtained in a yield of 24%. The object product showed the following infrared absorption maxima as a KBr-tablet and the following ultraviolet absorption maximum in methanol:

IR Max.: 3320, 2900, 2825, 1780, 1700, 1640, 1520 and 1220 cm$^{-1}$
UV Max.: 252 nm.

The object product gave the following elementary analytical data:

|  | C (%) | H (%) | N (%) |
|---|---|---|---|
| Found: | 54.3 | 4.6 | 11.4 |
| Calcd. as $C_{22}H_{22}N_4O_7S$: | 54.32 | 4.56 | 11.52 | corresponding to the chemical structure shown below:

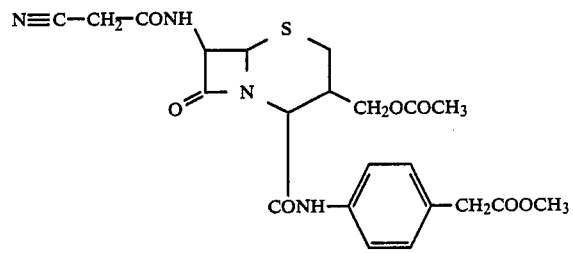

EXAMPLE 9

Production of N-(4-carbomethoxymethylcarbamoylphenyl)-[7-(2-cyanoacetamido)cephalosporanic]amide In the same procedures as in Example 3 except for using 339 mg of 7-(2-cyanoacetamido)cephalosporanic acid instead of 423.4 mg of 7-(4-pyridylthioacetamido)-cephalosporanic acid in Example 3 and stirring the solution for 15 hours at 30° C. instead of stirring the solution for 24 hours at 20° C. in Example 3, 198 mg of crystals of the object product melting at 220° to 221° C. in a yield of 37%.

The thus obtained object product showed the following infrared absorption maxima as a KBr-tablet and the following ultraviolet absorption maximum in methanol:

IR Max: 3350, 2925, 2825, 1790, 1705, 1640, 1530 and 1230 cm$^{-1}$
UV Max.: 268 nm.

The elementary analytical data of the object compound are as follows:

|  | C (%) | H (%) | N (%) |
|---|---|---|---|
| Found: | 52.1 | 4.3 | 13.1 |
| Calcd. as $C_{23}H_{23}N_5O_8S$: | 52.17 | 4.38 | 13.22 | corresponding to the chemical structure shown below:

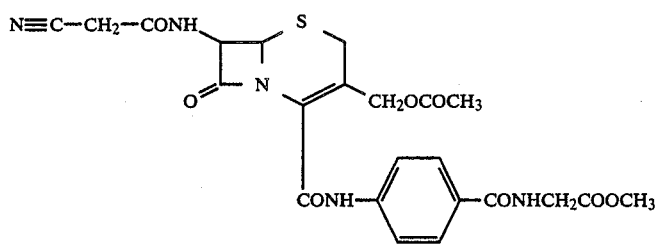

EXAMPLE 10

Production of N-(4-methylphenyl)-[7-(2-cyanoacetamido)caphalosporanic]amide

In the same procedure as in Example 3 except for using 339 mg of 7-(2-cyanoacetamido)cephalosporanic acid and 107.5 mg of toluidine, respectively instead of 423.4 mg of 7-(4-pyridylthioacetamido)cephalosporanic acid and 208.2 mg of methyl 4-aminohippurate in Example 3, 90 mg of the object product as crystals melting at 101° to 108° C. in a yield of 21%.

The thus obtained object product showed the following infrared absorption maxima as a KBr-tablet and the following ultraviolet absorption maximum in methanol;

IR Max.: 3350, 2925, 2850, 1780, 1700, 1640, 1530 and 1520 cm$^{-1}$

UV Max.: 244 nm.

The elementary analytical data of the object product were as follows:

|  | C (%) | H (%) | N (%) |
|---|---|---|---|
| Found: | 59.9 | 4.6 | 13.1 |
| Calcd. as $C_{20}H_{20}N_4O_5S$: | 56.06 | 4.71 | 13.07 | corresponding to the chemical structure shown below:

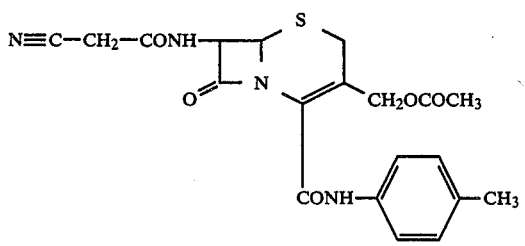

EXAMPLE 11

Production of N-(nicotinic amido)-[7-(2-cyanoacetamido)cephalosporanic]amide

Into 30 ml of tetrahydrofuran, 339.3 mg of 7-(2-cyanoacetamido)cephalosporanic acid, 137.1 mg of 6-aminonicotinic amide and 206 mg of N,N'-dicyclohexylcarbodiimide were dissolved, and the thus formed solution was stirred for 24 hours at room temperature. After removing the crystals in the reaction mixture, the remaining solution was dried under a reduced pressure, and acetone was added to the residue. After removing the matters insoluble in acetone, the remaining liquid was dried under a reduced pressure to obtain a crude product, which was recrystallized from a mixture of acetone and n-hexane to obtain 17 mg of the object product as pale yellow powdery crystals melting at 168° to 169° C. in a yield of 3.7%. The object product showed the following infrared absorption maxima as a KBr-tablet and the following ultraviolet absorption maximum in methanol:

IR Max.: 3480, 3370, 3240, 2950, 1775, 1750, 1700, 1670, 1540, 1400, 1360 and 1235 cm$^{-1}$ UV Max.: 265 nm The elementary analytical data of the object product were as follows:

|  | C (%) | H (%) | N (%) |
|---|---|---|---|
| Found: | 49.9 | 3.7 | 18.4 |
| Calcd. as $C_{19}H_{18}N_6O_6S$: | 49.78 | 3.96 | 18.33 | corresponding to the chemical structure as follows:

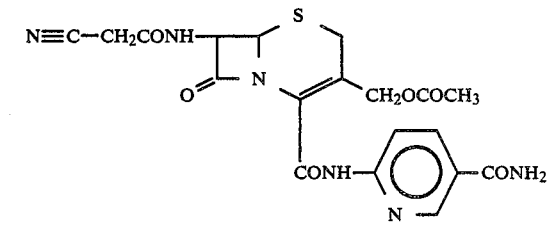

EXAMPLE 12

Production of N-(4-carboxyphenyl)-{7-(1-1H-tetrazolylacetamido)-3-[2-(5-methyl-1,3,4-thiadiaziolyl)thiomethyl]-3-cephem-4-carboxylic}amide In the same procedures as in Example 1 except for using 476 mg of sodium 7-(1-1H-tetrazolylacetamido)-3-[2-(5-methyl-1,3,4-thiadiazolyl)thiomethyl]-3-cephem-4-carboxylate and 137 mg of 4-aminobenzoic acid, respectively instead of 445 mg of sodium 7-(4-pyridylthioacetamido)cephalosporanate and 151 mg of methyl 4-aminobenzoate, 58 mg of the object product as crystals melting at 123° to 125° C. were obtained in a yield of 10%. The ultraviolet absorption spectrum of the object product showed an absorption maximum at 271 nm in methanol.

The elementary analytical data of the object product were as follows:

|  | C (%) | H (%) | N (%) |
| --- | --- | --- | --- |
| Found: | 43.8 | 3.3 | 21.8 |
| Calcd. as $C_{21}H_{19}N_9O_5S_3$: | 43.97 | 3.34 | 21.98 | corresponding to the chemical structure as follows:

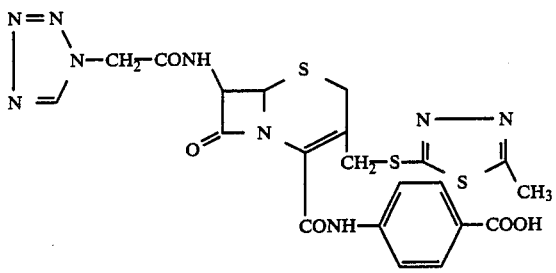

EXAMPLE 13

Production of N-(4-carbomethoxyphenyl)-{7-(1-1H-tetrazolylacetamido)-3-[2-(5-methyl-1,3,4-thiadiazolyl)thiomethyl]-3-cephem-4-carboxylic}amide In the same procedures as in Example 1 except for using 476 mg of 7-(1-1H-tetrazolylacetamido)-3-[2-(5-methyl-1,3,4-thiadiazolyl)thiomethyl]-3-cephem-4-carboxylic acid instead of 445 mg of sodium 7-(4-pyridylthioacetamido)cephalosporanate in Example 1 and stirring the mixture for 24 hours at 25° C. instead of 30 hours at 20° C. in Example 1, 408 mg of the object product were obtained as crystals melting at 115° to 118° C. in a yield of 82%. The object product showed the following infrared absorption maxima as a KBr-tablet and the following ultraviolet absorption maximum in methanol:

IR Max.: 3305, 2925, 2805, 1775, 1700, 1620, 1600, 1530 and 1280 $cm^{-1}$

UV Max.: 278 nm

The elementary analytical data of the object product were as follows:

|  | C (%) | H (%) | N (%) |
| --- | --- | --- | --- |
| Found: | 44.9 | 3.6 | 21.4 |
| Calcd. as $C_{22}H_{21}N_9O_5S_3$: | 44.97 | 3.60 | 21.45 | corresponding to the chemical structure as follows:

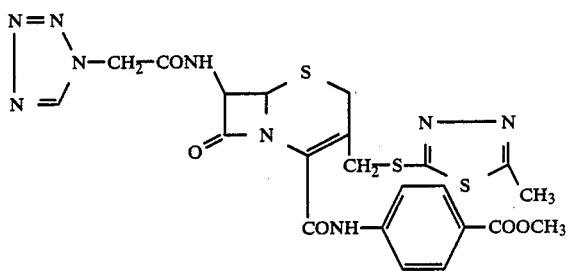

Example 14

Production of N-(4-carbomethoxymethylphenyl)-{7-(1-1H-tetrazolylacetamido)-3-[2-(5-methyl-1,3,4-thiadiazolyl)thiomethyl]-3-cephem-4-carboxylic}amide In the same procedures as in Example 1 except for using 476 mg of 7-(1-1H-tetrazolylacetamido)-3-[2-(5-methyl-1,3,4-thiadiazolyl)thiomethyl]-3-cephem-4-carboxylic acid and 165 mg of methyl 4-aminophenylacetate, respectively instead of 445 mg of sodium 7-(4-pyridylthioacetamido)cephalosporanate and 151 mg of methyl 4-aminobenzoate in Example 1 and stirring for 30 hours at 15° C. instead of 30 hours at 20° C. in Example 1, 119 mg of the object product were obtained as crystals melting at 112° to 114° C. in a yield of 19%. The object product showed the following infrared absorption maxima as a KBr-tablet:

3340, 2940, 2850, 1780, 1690, 1630, 1535 and 1240 $cm^{-1}$.

The elementary analytical data of the object product were as follows:

|  | C (%) | H (%) | N (%) |
| --- | --- | --- | --- |
| Found: | 44.9 | 3.9 | 22.7 |
| Calcd. as $C_{23}H_{24}N_{10}O_5S_3$: | 44.80 | 3.92 | 22.71 | corresponding to the chemical structure shown below:

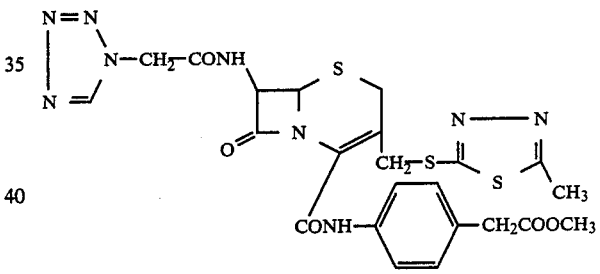

EXAMPLE 15

Production of N-(4-carbomethoxymethylcarbamoylphenyl)-{7-(1-1H-tetrazolylacetamido)-3-[2-(5-methyl-1,3,4-thiadiazolyl)thiomethyl]-3-cephem-4-carboxylic}amide In the same procedures as in Example 3 except for using 476 mg of 7-(1-1H-tetrazolylacetamido)-3-[2-(5-methyl-1,3,4-thiadiazolyl)thiomethyl]-3-cephem-4-carboxylic acid and 208.9 mg of methyl 4-aminohippurate, respectively instead of 423.4 mg of 7-(4-pyridylthioacetamido)cephalosporanic acid and 208.2 mg of methyl 4-aminohippurate in Example 3 and stirring the mixture for 30 hours at 5° C. instead of 24 hours at 20° C., 250 mg of the object product were obtained as crystals melting at 119° to 121° C. in a yield of 39%. The object product showed the following infrared absorption maxima as a KBr-tablet, and the following ultraviolet absorption maximum in methanol:

IR Max.: 3325, 3280, 2925, 2850, 1780, 1680, 1620, 1560 and 1540 $cm^{-1}$

UV Max.: 275 nm

The elementary analytical data of the object product were as follows:

| | C (%) | H (%) | N (%) |
|---|---|---|---|
| Found: | 44.6 | 3.7 | 21.7 |
| Calcd. as $C_{24}H_{24}N_{10}O_6S_3$: | 44.71 | 3.75 | 21.72 | corresponding to the chemical structure shown below:

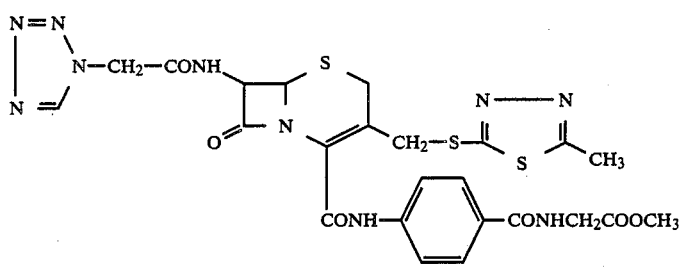

EXAMPLE 16

Production of N-(4-methylphenyl)-{7-(1-1H-tetrazolylacetamido)-3-[2-(5-methyl-1,3,4-thiadiazolyl)thiomethyl]-3-cephem-4-carboxylic}amide In the same procedures as in Example 3 except for using 476 mg of 7-(1-1H-tetrazolylacetamido)-3-[2-(5-methyl-1,3,4-thiadiazolyl)thiomethyl]-3-cephem-4-carboxylic acid and 107 mg of toluidine, respectively instead of 423.4 mg of 7-(4-pyridylthioacetamido)caphalosporanic acid and 208.2 mg of methyl 4-aminohippurate in Example 3, 314 mg of the object product were obtained as crystals melting at 124° to 127° C. in a yield of 58%. The object product showed the following infrared absorption maxima as a KBr-tablet, and the following ultraviolet absorption maxima in methanol:

IR Max.: 3325, 3020, 2840, 1775, 1770, 1625, 1530 and 1240 cm$^{-1}$

UV Max.: 272 nm

The elementary analytical dta of the object product were as follows:

| | C (%) | H (%) | N (%) |
|---|---|---|---|
| Found: | 46.4 | 3.7 | 23.1 |
| Calcd. as $C_{21}H_{21}N_9O_3S_3$: | 46.40 | 3.89 | 23.19 | corresponding to the chemical structure shown below:

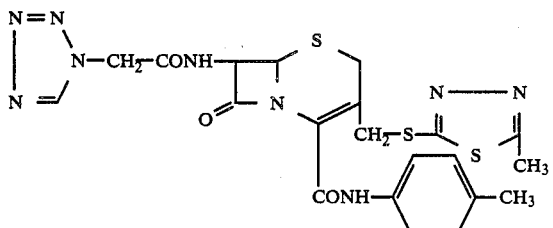

EXAMPLE 17

Production of N-[beta-(4-hydroxyphenyl)ethyl]-{7-(1-1H-tetrazolylacetamido)-3-[2-(5-methyl-1,3,4-thiadiazolyl)thiomethyl]-3-cephem-4-carboxylic}amide A solution prepared by dissolving 4.54 g of 7-(1-1H-tetrazolylacetamido)-3-[2-(5-methyl-1,3,4-thiadiazolyl)-thiomethyl]-3-cephem-4-carboxylic acid, 1.37 g of tyramine and 2.10 g of N,N'-dicyclohexylcarbodiimide in 70 ml of tetrahydrofuran was stirred for 24 hours at 15° C. After collecting the crystals formed in the reaction mixture by filtration thereof, the crystals were washed two times with each 30 ml of tetrahydrofuran, and recrystallized from a mixture of dimethylformamide and ethanol to obtain 2.6 g of the object product as pale yellow powdery crystals melting at 147° to 149° C. in a yield of 45%. The thus obtained object product showed the following infrared absorption maxima as a KBr-tablet and the following ultraviolet absorption maxima in methanol:

IR Max.: 3250, 1760, 1660, 1593, 1378 and 1235 cm$^{-1}$

UV Max.: 222 and 275 nm

The elementary analytical data of the object product were as follows:

| | C (%) | H (%) | N (%) |
|---|---|---|---|
| Found: | 46.1 | 4.1 | 22.0 |
| Calcd. as $C_{22}H_{23}N_8O_6S_3$: | 46.07 | 4.01 | 21.99 | corresponding to the chemical structure as follows:

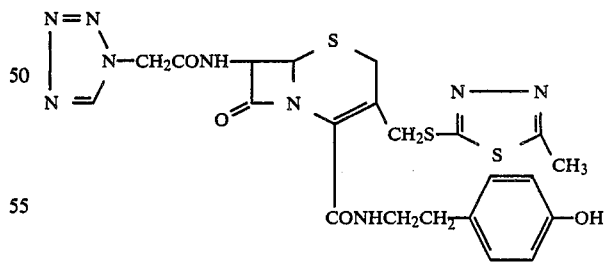

EXAMPLE 18

Production of N-(6-nicotinic amide)-{7-(1-1h-tetrazolylacetamido)-3-[2-(5-methyl-1,3,4-thiadiazolyl)thiomethyl]-3-cepehem-4-carboxylic}amide A solution prepared by dissolving 454.49 mg of 7-(1-1H-tetrazolylacetamido)-3-[2-(5-methyl-1,3,4-thiadiazolyl)thiomethyl]-3-cephem-4-carboxylic acid, 137.1 mg of 6-aminonicotinic amide and 206 mg of N,N'-dicyclohexylcarbodiimide into 30 ml of tetrahydrofuran was stirred for 24 hours at room temperature. After removing the crystals formed in the reaction mixture by centrifugation, the remaining liquid was dried under a reduced pressure to obtain a crude product, which was recrystallized from a mixture of acetone and n-hexane to obtain 39 mg of the object product as pale orange powdery crystals melting at 136° to 137° C. in a yield of 6.8%.

The thus obtained object product showed the following infrared absorption maxima as a KBr-tablet and the following ultraviolet absorption maximum in methanol.

IR Max.: 3370, 2950, 2875, 1760, 1680, 1630, 1575, 1385 and 1245 cm$^{-1}$

UV Max.: 268 nm

The elementary analytical data of the object product were as follows:

|  | C (%) | H (%) | N (%) |
|---|---|---|---|
| Found: | 41.6 | 3.2 | 26.9 |
| Calcd. as $C_{20}H_{19}N_{11}O_4S_3$: | 41.88 | 3.34 | 26.86 | corresponding to the chemical structure shown below:

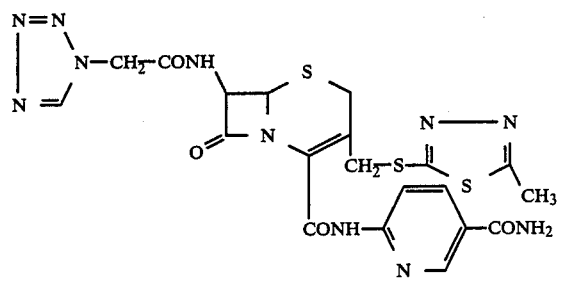

EXAMPLE 19

Effects of the present compound on intestinal bacteria

Each of the present compounds respectively produced in Examples 1 to 18 was orally administered continuously for 2 days at a daily dose rate of 500 mg/kg body weight to each of five female ICR mice of each group after 6 weeks of their birth.

Each of the two fecal specimens respectively collected from each mouse before and after one day of the administration was diluted with 100 times by weight of an anaerobic diluent (a phosphoric acid buffer solution) and was ground in a mortar, and 0.1 ml of the thus ground material was smeared on each of the following culture media for the following bacteria, and the thus inoculated culture media were incubated under the following conditions. Thereafter, the number of the following bacteria in each of the thus cultured media was determined.

| Culture medium and conditions of culture | | |
|---|---|---|
| Bacterial species | Culture medium | Conditions in culture |
| Escherichia coli | DHL agar | 37° C., one day, aerobic |
| Pseudomonas aeruginosa | NAC agar | 37° C., one day, aerobic |
| a species of Streptococcus | TATAC agar | 37° C., one day, aerobic |
| a species of Lactobacillus | LBS agar | 37° C., 5 days, anaerobic |
| Lactobacillus bifidus | BS agar | 37° C., 5 days, anaerobic |
| a species of Bacteroides | NBGT agar | 37° C., 5 days, anaerobic |

The results are shown in Table which also shows the results of the same type of tests using each of the publicly known cephalosporins such as CEPHAPIRIN, CEFALEXIN, sodium 7-(2-cyanoacetamido)cephalosporanate and SODIUM CEFAZORIN instead of each of the present compounds.

TABLE 1

Number of Intestinal Bacterial Species before and after the administration

Unit: $Log_{10}$ (number of bacteria/g feces)

| Test No. | Before or after administration | Compound prepared in Example | Escherichia coli | Pseudomonas aeruginosa | A sp. of Streptococcus | A sp. of Lactobacillus | Lactobacillus bifidus | A sp. of Bacterioides |
|---|---|---|---|---|---|---|---|---|
| 1-0 | before | — | 6.4 | <3.0 | 6.8 | 9.0 | 8.3 | 8.2 |
| 1-1 | after | Ex. 1 | 6.9 | <3.0 | 6.7 | 9.1 | 8.4 | 8.8 |
| 1-2 | after | Ex. 2 | 6.5 | <3.0 | 6.6 | 9.0 | 8.6 | 8.7 |
| 1-3 | after | Ex. 3 | 6.5 | <3.0 | 6.7 | 9.1 | 8.5 | 8.1 |
| 1-4 | after | Ex. 4 | 6.6 | <3.0 | 6.8 | 8.9 | 8.3 | 8.3 |
| 1-5 | after | Ex. 5 | 6.5 | <3.0 | 6.7 | 8.9 | 8.4 | 8.4 |
| 1-6 | after | Ex. 6 | 6.7 | <3.0 | 6.7 | 9.0 | 8.6 | 8.7 |
| 1-7 | after | CEPHAPIRIN[1] | 9.0 | <3.0 | 9.1 | 4.1 | 9.1 | 8.5 |
| 1-8 | after | CEFALEXIN[2] | 9.2 | <3.0 | 8.5 | 4.0 | 8.0 | 8.1 |
| 2-1 | after | Ex. 7 | 6.5 | <3.0 | 6.7 | 9.0 | 8.3 | 8.7 |
| 2-2 | after | Ex. 8 | 6.6 | <3.0 | 6.6 | 9.1 | 8.4 | 8.9 |
| 2-3 | after | Ex. 9 | 6.5 | <3.0 | 6.7 | 8.9 | 8.4 | 8.5 |
| 2-4 | after | Ex. 10 | 6.8 | <3.0 | 6.8 | 9.0 | 8.2 | 8.9 |
| 2-5 | after | Ex. 11 | 6.8 | <3.0 | 6.7 | 9.1 | 8.2 | 8.6 |
| 2-6 | after | Compound X[3] | 9.0 | <3.0 | 9.1 | 4.6 | 6.0 | 8.2 |
| 3-1 | after | Ex. 12 | 6.5 | <3.0 | 6.7 | 8.9 | 8.2 | 8.8 |
| 3-2 | after | Ex. 13 | 6.4 | <3.0 | 6.6 | 9.0 | 8.4 | 8.7 |
| 3-3 | after | Ex. 14 | 6.4 | <3.0 | 6.6 | 9.0 | 8.2 | 8.4 |
| 3-4 | after | Ex. 15 | 6.5 | <3.0 | 6.8 | 9.1 | 8.2 | 8.2 |
| 3-5 | after | Ex. 16 | 6.5 | <3.0 | 6.5 | 9.2 | 8.3 | 8.1 |
| 3-6 | after | Ex. 17 | 6.4 | <3.0 | 6.9 | 9.0 | 8.4 | 8.1 |
| 3-7 | after | Ex. 18 | 6.4 | <3.0 | 6.9 | 9.0 | 8.4 | 8.1 |

TABLE 1-continued

| | | | Number of Intestinal Bacterial Species before and after the administration | | | | | |
|---|---|---|---|---|---|---|---|---|
| | | | | | | Unit: $Log_{10}$ (number of bacteria/g feces) Bacterial species | | |
| Test No. | Before or after administration | Compound prepared in Example | Escherichia coli | Pseudomonas aeruginosa | A sp. of Streptococcus | A sp. of Lactobacillus | Lactobacillus bifidus | A sp. of Bacterioides |
| 3-8 | after | SODIUM CEFAZORIN[(4)] | 8.9 | <3.0 | 8.6 | 4.0 | 9.1 | 7.3 |

Notes:
[(1)] CEPHAPIRIN: 7-(4-pyridylthioacetamido)cephalosporanic acid
[(2)] CEFALEXIN: 7-(D-alpha-amino-alpha-phenylacetamido)-3-methyl-3-cephem-4-carboxylic acid
[(3)] Compound X: sodium 7-(2-cyanoacetamido)cephalosporanate
[(4)] SODIUM CEFAZORIN: Sodium 7-(1-1H—tetrazolylacetamido)-3-[2-(5-methyl-1,3,4-thiadiazolyl)thiomethyl]-3-cephem-4-carboxylate As are seen in Table 1, in the group administered with every one of the publicly known cephalosporins, the number of *Escherichia coli* became larger than before administration, and on the other hand, in the group administered with every one of the present compounds produced in Examples 1 to 18, the number of *Escherichia coli* did not show any conspicuous change as compared to that before administration. In addition, in the group administered with every one of the publicly known cephalosporins, the number of the species of Lactobacillus became smaller than that before administration, on the other hand, the group administered with every one of the present compounds produced in Examples 1 to 18, the number of the species of Lactobacillus showed no change as compared to that before administration.

Namely, among the present compounds, at least every one of those produced in Examples 1 to 18 does not give any conspicuous effects on the major bacteria habitually present in the intestinal tracts of the mouse.

EXAMPLE 20

Determination of the antibacterial activity of the present compound

Determination of the antibacterial activity of the present compound produced in Examples 1 to 18, respectively was carried out according to the standard procedures of Japan Society of Chemotherapy for finding MIC (the minimum concentration of a specimen to inhibit the growth of a species of bacteria).

A series of diluted solutions of each of the present compound were mixed with 9 times by weight of Mueller-Hinton's culture medium as the culture medium for determining the sensitivity of a bacterial species, and flat agar culture plates were prepared by using the thus obtained mixture.

Each of the liquids respectively containing one of the bacterial species shown in Table 2 was smeared onto each of the thus prepared flat agar culture plates with a platinum loop, in length of about 2 cm, and the thus treated plates were incubated for 18 to 24 hours at 37° C. Thereafter, by observing the growth state of each bacterial species on the cultured plates, the minimum concentration of each compound completely inhibiting the growth of each bacterial species was found.

Table 2 shows the results as MIC.

TABLE 2

| MIC (minimum growth inhibiting concentration) | | |
|---|---|---|
| | | Unit: microgram/ml |
| Present compound produced in Example | MIC against | |
| | Escherichia coli | Staphylococcus aureus |
| 1 | ≧100 | ≧12.5 |
| 2 | ≧100 | ≧50 |

TABLE 2-continued

| MIC (minimum growth inhibiting concentration) | | |
|---|---|---|
| | | Unit: microgram/ml |
| Present compound produced in Example | MIC against | |
| | Escherichia coli | Staphylococcus aureus |
| 3 | ≧100 | ≧50 |
| 4 | ≧100 | ≧100 |
| 5 | ≧100 | ≧100 |
| 6 | ≧100 | ≧100 |
| 7 | ≧100 | ≧100 |
| 8 | ≧100 | ≧100 |
| 9 | ≧100 | ≧100 |
| 10 | ≧100 | ≧100 |
| 11 | ≧100 | ≧100 |
| 12 | ≧25 | ≧1.56 |
| 13 | ≧100 | ≧12.5 |
| 14 | ≧100 | ≧12.5 |
| 15 | ≧100 | ≧12.5 |
| 16 | ≧100 | ≧12.5 |
| 17 | ≧3.12 | ≧0.78 |
| 18 | ≧100 | ≧12.5 |

EXAMPLE 21

Model experiment for verifying the activation in living body

The following composition (hereinafter referred to as S-9 mix) was prepared and used as a metabolism-activating enzyme while using rat-liver homogenate (S-9) as a component:

Components in 1 ml of the composition 0.5 ml of S-9 (rat-liver homogenate)
3.3 micromol of potassium chloride
8 micromol of magnesium chloride hexahydrate
5 micromol of glucose hexaphosphate
4 micromol of NADH
4 micromol of NADPH
0.5 ml of 0.2M phosphoric buffer solution of pH of 7.4

A mixture of 0.1 ml of the test liquid containing each of the present compounds respectively produced in Examples 1 to 18 and 0.9 ml of S-9 mix or 0.9 ml of a control (0.1M phosphoric acid buffer solution) was shaken for 20 min at 37° C. to prepare each reaction liquid.

A preliminarily prepared culture medium containing $10^8$ cells of *Staphylococcus aureus* IAM 1011/ml of Mueller-Hinton's culture medium for 18 hours at 37° C. was mixed with 50 times by weight of new Mueller-Hinton's agar culture medium, and flat culture plates were prepared while using the thus prepared mixture.

A penicillin cup of 8 mm in diameter was placed on each of the flat culture plates, and after placing 0.1 ml of each of the above-mentioned reaction liquid, the plates were incubated for 18 hours at 37° C. Thereafter, the diameter of each bacteria's growth-inhibition circle formed around the penicillin cup was measured. The results are shown in Table 3.

For reference, the same procedures were carried out while using each substituted cephalosporanic acid used as the starting substance for producing each of the present compounds without adding S-9 mix, and the diameter of growth-inhibition circle formed by each substituted cephalosporanic acid was also measured, and the percentage of the diameter of growth-inhibition circle due to each of the present compounds to that due to each of the substituted cephalosporanic acid was shown in Table 3.

TABLE 3

| Present compound produced in Example | $(d_1/d_2) \times 100^{(1)}$ | |
|---|---|---|
| | without addition of S-9 mix | with addition of S-9 mix |
| Example 1 | − | ++ |
| 2 | − | + |
| 3 | − | ++ |
| 4 | − | + |
| 5 | − | ++ |
| 6 | − | + |
| 7 | − | + |
| 8 | − | + |
| 9 | − | + |
| 10 | − | ++ |
| 11 | − | + |
| 12 | ± | ++ |
| 13 | − | + |
| 14 | − | ++ |
| 15 | − | + |
| 16 | − | + |
| 17 | ± | +++ |
| 18 | − | + |

Note
$^{(1)}d_1$ is the diameter of growth-inhibition circle due to each of the present compounds, and $d_2$ is the diameter of growth-inhibition circle due to each of substituted cephalosporanic acid used for producing each of the present compounds, and the signs in Table 3 correspond to the respective percentage, $(d_1/d_2) \times 100$, shown below:

| Sign | Range of the percentage |
|---|---|
| − | 0 |
| ± | 0 to 1% |
| + | 1 to 33% |
| ++ | 33 to 66% |
| +++ | 66 to 100% |

EXAMPLE 22

Effectiveness of the present compound in treatment of an experimental infectious disease in mouse (1) Disease due to infection of *Escherichia coli*

Each mouse of the two groups (20 animals/group) of ddY SPE mice was inoculated with $1.4 \times 10^8$ cells of *Escherichia coli* IFO 12734 intraperitoneally, and then, each mouse of the one of the two groups was administered orally with one of the present compounds, namely the compound produced in Example 5, 10 or 13, two times just after and 4 hours after the inoculation, while the 20 mice of the other group were not administered. On observing the two groups of SPE mice for 7 days after the inoculation, it was found that while all the inoculated and not-administered mice died within the 7 days, (1) more than 60% of the mice administered with the compound produced in Example 5 were alive on the 7th day of inoculation, (2) more than 80% of the mice administered with the compound produced in Example 10 and (3) more than 80% of the mice administered with the compound produced in Example 13 were alive on the 7th day of inoculation.

(2) Disease due to infection of *Staphylococcus aureus*

Each mouse of the two groups (20 animals/group) of ddY SPE mice was inoculated with $2.3 \times 10^8$ cells of *Staphylococcus aureus* IAM 1011 intraperitoneally, and then, each mouse of the one of the two groups was administered orally with one of the present compounds, namely the compound produced in Example 5, 10 or 13, two times just after and 4 hours after the inoculation, while the 20 mice of the other group were not administered. On observing the two groups of SPE mice for 7 days after the inoculation, it was found that while all the mice inoculated and not-administered died within 3 days after the inoculation, (1) more than 65% of the mice administered with the compound produced in Example 5, (2) more than 85% of the mice administered with the compound produced in Example 10 and (3) more than 60% of the mice administered with the compound produced in Example 13 were alive on the 7th day of inoculation.

EXAMPLE 23

Examples of preparation of pharmaceutical composition comprising at least one of the present compounds as an active ingredient (1) Tablets for oral administration:
Recipe of the tablet (200 mg/tablet)
175 mg of the compound produced in Example 1
16 mg of lactose
5 mg of starch
3 mg of hydroxypropylcellulose
1 mg of magnesium stearate At first, lactose and the present compound were mixed, and after adding an aqueous solution of hydroxypropylcellulose into the mixture, the aqueous mixture was kneaded, dried and pulverized. After admixing magnesium stearate preliminarily dispersed into starch with the pulverized mixture, the whole mixture was subjected to a conventional tablet machine to obtain the tablets.

(2) Granular composition for oral administration:
Recipe of the granular composition:
176 mg of the compound produced in Example 2
16 mg of lactose
4 mg of starch
4 mg of hydroxypropylcellulose After mixing the present compound, starch and lactose, aqueous solution of hydroxypropylcellulose was added to the mixture, and the whole mixture was mixed again, dried and pulverized. After sifting the pulverized mixture with two standard Taylor sieves #12 mesh and #48 mesh, the granular composition passing through #12 mesh standard Taylor sieve and stopping on #48 mesh standard Taylor sieve.

What is claimed is:
1. A substituted cephalosporin represented by the formula:

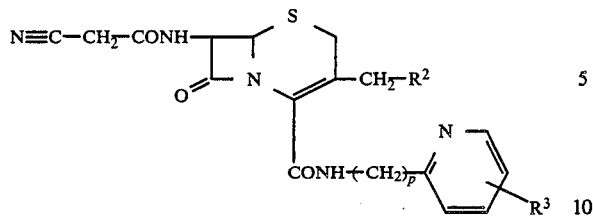

wherein $R^2$ represents a hydrogen atom, an acetoxy group or a 5-methyl-1,3,4-thiadiazol-2-yl-thio group; p is 0, 1 or 2 and $R^3$ represents a hydrogen atom, a hydroxyl group, a carbamoyl group, an alkyl group having 1 to 4 carbon atoms or $—(CONH)_m(CH_2)_n—COOH$ wherein m is 0 or 1, n is 0, 1 or 2 and the carboxyl group may have been converted to a salt or an ester thereof.

2. A compound according to claim 1, represented by the formula:

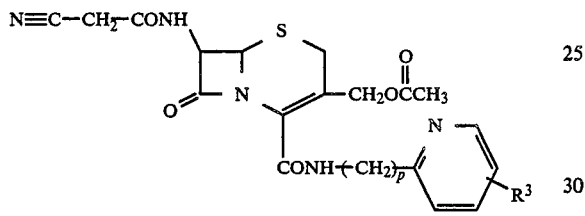

wherein p and $R^3$ respectively represent the same as in said formula in claim 1.

3. A compound according to claim 2, represented by the formula:

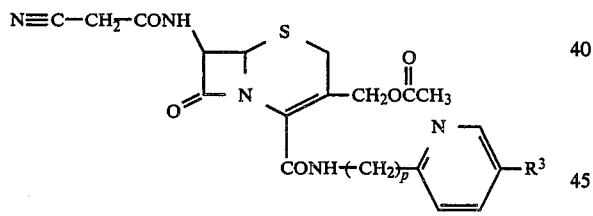

wherein p is 0, 1 or 2 and $R^3$ represents a carbamoyl group, an alkyl group having 1 to 4 carbon atoms or $—(CONH)_m(CH_2)_n—COOH$ wherein m is 0 or 1, n is 0, 1 or 2 and the carboxyl group may have been converted into a salt or an ester thereof.

4. N-(nicotinic amide)-(7-(2-cyanoacetamido)cephalosporanic)amide represented by the formula:

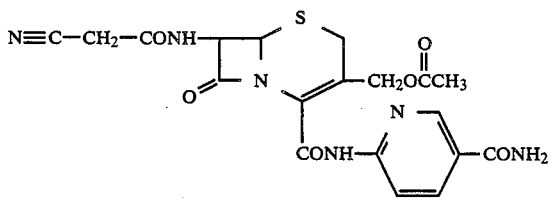

5. A pharmaceutical composition in dosage unit form comprising an effective amount of a compound represented by the formula:

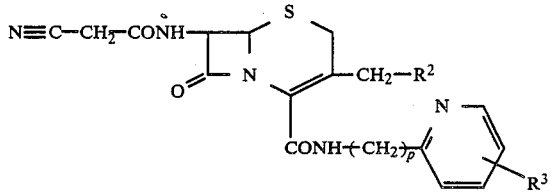

wherein $R^2$ represents a hydrogen atom, an acetoxy group or a 5-methyl-1,3,4-thiadiazol-2-yl-thio group; p is 0, 1 or 2 and $R^3$ represents a hydrogen atom, a hydroxyl group, a carbamoyl group, an alkyl group having 1 to 4 carbon atoms or $—(CONH)_m(CH_2)_n—COOH$ wherein m is 0 or 1, n is 0, 1 or 2 and the carboxyl group may have been converted into a pharmaceutically acceptable salt or $C_1$ to $C_4$-alkyl ester thereof, as an effective component, and a pharmaceutically acceptable carrier thereof.

6. A pharmaceutical composition according to claim 5, wherein said compound is represented by the formula:

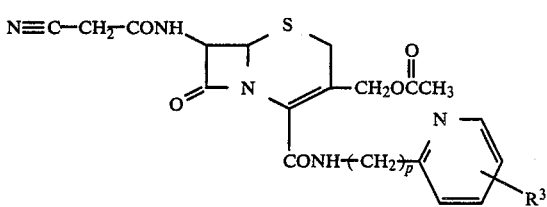

wherein p and $R^3$ respectively represent the same as in said formula in claim 5.

7. A pharmaceutical composition according to claim 6, wherein said compound is represented by the formula:

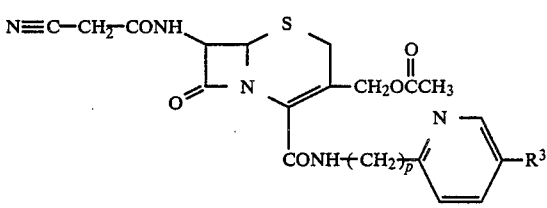

wherein p is 0, 1 or 2 and $R^3$ represents a carbamoyl group, an alkyl group having 1 or 4 carbon atoms or $—(CONH)_m(CH_2)_n—COOH$ wherein m is 0 or 1, n is 0, 1 or 2 and the carboxyl group may have been converted into a pharmaceutically acceptable salt or $C_1$ to $C_4$-alkyl ester thereof.

8. A pharmaceutical composition according to claim 7, wherein said compound is N-(nicotinic amide)-(7-(2-cyanoacetamido)-cephalosporanic)amide represented by the formula:

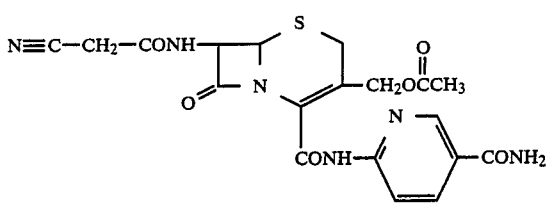

9. A method for treatment of an infectious disease caused by bacteria, comprising administering an effective antibacterial amount of a compound represented by the formula:

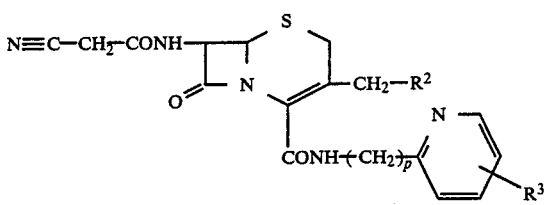

wherein $R^2$ represents a hydrogen atom, an acetoxy group or a 5-methyl-1,3,4-thiadiazol-2-yl-thio group; p is 0, 1 or 2 and $R^3$ represents a hydrogen atom, a hydroxyl group, a carbamoyl group, an alkyl group having 1 to 4 carbon atoms or $-(CONH)_m(CH_2)_n-COOH$ wherein m is 0 or 1, n is 0, 1 or 2 and the carboxyl group may have been converted into a pharmaceutically acceptable salt of $C_1$ to $C_4$-alkyl ester thereof, to the host suffering from said disease.

10. A method according to claim 9, wherein said compound is represented by the formula:

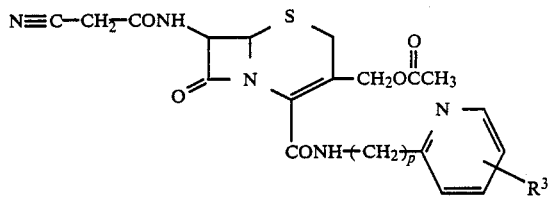

wherein p, X and $R^3$ respectively represent the same as in said formula in claim 9.

11. A method according to claim 10, wherein said compound is represented by the formula:

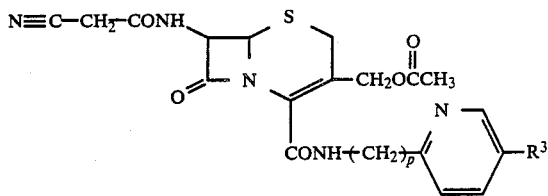

wherein p is 0, 1 or 2 and $R^3$ represents a carbamoyl group, an alkyl group having 1 to 4 carbon atoms or $-(CONH)_m(CH_2)_n-COOH$ wherein m is 0 or 1, n is 0, 1 or 2 and the carboxyl group may have been converted into a pharmaceutically acceptable salt or $C_1$ to $C_4$-alkyl ester thereof.

12. A method according to claim 11, wherein said compound is N-(nicotinic amide)-(7-(2-cyanoacetamido)cephalosporanic)amide represented by the formula:

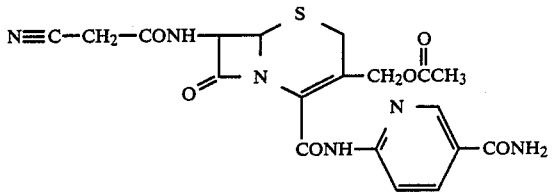

* * * * *